(12) United States Patent
Carrasco

(10) Patent No.: US 7,211,097 B2
(45) Date of Patent: May 1, 2007

(54) SANITARY COUPLING FOR NEEDLE AND MECHANIZED MICROPIGMENTATION AND TATTOOING PUNCH

(75) Inventor: Mario Gisbert Carrasco, Madrid (ES)

(73) Assignee: Goldeneye, S.L., Madrid (ES)

( * ) Notice: Subject to any disclaimer, the term of this patent is extended or adjusted under 35 U.S.C. 154(b) by 274 days.

(21) Appl. No.: 10/785,405

(22) Filed: Feb. 25, 2004

(65) Prior Publication Data

US 2005/0055042 A1    Mar. 10, 2005

(30) Foreign Application Priority Data

Sep. 10, 2003  (ES) ............................... 200300524

(51) Int. Cl.
*A61B 17/34* (2006.01)

(52) U.S. Cl. ................................................. 606/186
(58) Field of Classification Search ........ 606/184–189, 606/116; 604/19, 22, 221, 206, 226, 187–197, 604/240–241, 264, 110; 81/9.22
See application file for complete search history.

(56) References Cited

U.S. PATENT DOCUMENTS 5,741,290 A * 4/1998 Hsieh .......................... 606/186
5,776,158 A * 7/1998 Chou .......................... 606/186

* cited by examiner

*Primary Examiner*—Anh Tuan Nguyen
*Assistant Examiner*—Tuan Van Nguyen
(74) *Attorney, Agent, or Firm*—Crowell & Moring LLP

(57) ABSTRACT

Sanitary coupling for needle and mechanized punch for micropigmentation and tattooing, having a threaded bolt that can perform shuttle micromovements of the protruding sheaf of the casing of the mechanized punch to which the base of a needle is coupled. The bolt passes through the casing of the mechanized punch through an orifice located in a prolongation and/or sleeve thereof. The base of the needle consists of a disc-like body which on one of its faces presents a threaded orifice for coupling to the thread of the bolt, and its edge is extended to form a complementary overlapping skirt around the form of the prolongation of the sleeve of the casing. On the other face of the disc-like body a protruding portion is centered where the non-dismountable body of the needle is attached. The edges of the disc-like body extend to form a housing for fluid collection.

3 Claims, 1 Drawing Sheet

SANITARY COUPLING FOR NEEDLE AND MECHANIZED MICROPIGMENTATION AND TATTOOING PUNCH

OBJECT OF THE INVENTION

The present invention relates to a sanitary coupling for needle and mechanized punch for micropigmentation and tattooing.

BACKGROUND OF THE INVENTION

At present, for application of micropigmentation and tattoo treatments, needles with one or several tips are used coupled interchangeably to a mechanized punch that comprises a pencil shaped casing for a better grip, with an internal motor and a transmission accessible from outside, to which the needle itself is coupled, and which imparts micromovement of the sheaf in the axial direction, which effects the introduction of the pigment under the skin, puncturing the skin.

The transmission where the needle is coupled consists of a bolt that passes through the casing through an orifice for that purpose, and in which the needle is housed or screwed by means of its own hollow end.

These configurations have two main drawbacks as, on the one hand, simple coupling by housing—the most widely used—often causes unwanted uncoupling of the needle, and on the other hand both the configurations by insertion and those with a screw fit can readily cause backflow of the pigment and other fluids, sometimes body fluids, because of the punctures made by the needle, towards the interior of the casing of the punch through the orifice through which transmission passes, which is a health problem and can even cause faults.

This is a great disadvantage of the current couplings as, although at present throwaway needles can be purchased, this does not prevent contamination of the interior of the casing by the passage of fluids, and even less so in the case of reusable needles, which need to be sterilized in an autoclave the use of which may be doubted by the patients.

DESCRIPTION OF THE INVENTION

The coupling of the invention serves for attaching a micropigmentation and/or tattooing needle to the mechanized punch responsible for the movement of the sheaf, in optimal sanitary conditions, as it prevents pigmentation or human fluids that are produced during application of the pigments from penetrating the interior of the casing of the punch and contaminating its interior or damaging its internal mechanism.

In accordance with the invention, the coupling consists of a threaded bolt that projects from the casing of the motorized punch through an orifice for the purpose, and a base of a needle that is fixed to said bolt such that it can be disassembled by unscrewing.

The bolt is coupled mechanically to a motor that generates shuttle movements therein in the axial direction, and protrudes from the casing through a hole that is placed in a protruding prolongation and/or sleeve, ideally cylindrical, thereof, passing centrally through its end.

On the other hand, the base of the needle consists of a body, ideally of plastic, with a disc-like form, the edges of which extend in the axial direction of the needle on both faces forming housing on one side and protruding from the same face, in a prolongation in a central position where the body of the needle is attached by a mount that cannot be disassembled, while on the opposite face of the prolonged edge forms a skirt that overlaps and covers the prolongation and/or sleeve of the casing of the mechanized punch. In the central part of this face, the disc-like body has a threaded hollow by which the threaded bolt of the mechanized punch is attached.

In this fashion, the threaded join avoids accidental uncoupling between the bolt and the base of the needle, while the housing, in cooperation with the overlap of the skirt of the base of the needle with the prolongation of the casing of the mechanized punch confines the fluids and/or prevents them from entering the area where the orifice of the prolongation of the casing is located, crossed by the bolt, preventing its interior from becoming contaminated.

DESCRIPTION OF A PRACTICAL EMBODIMENT OF THE INVENTION

Figure 1:
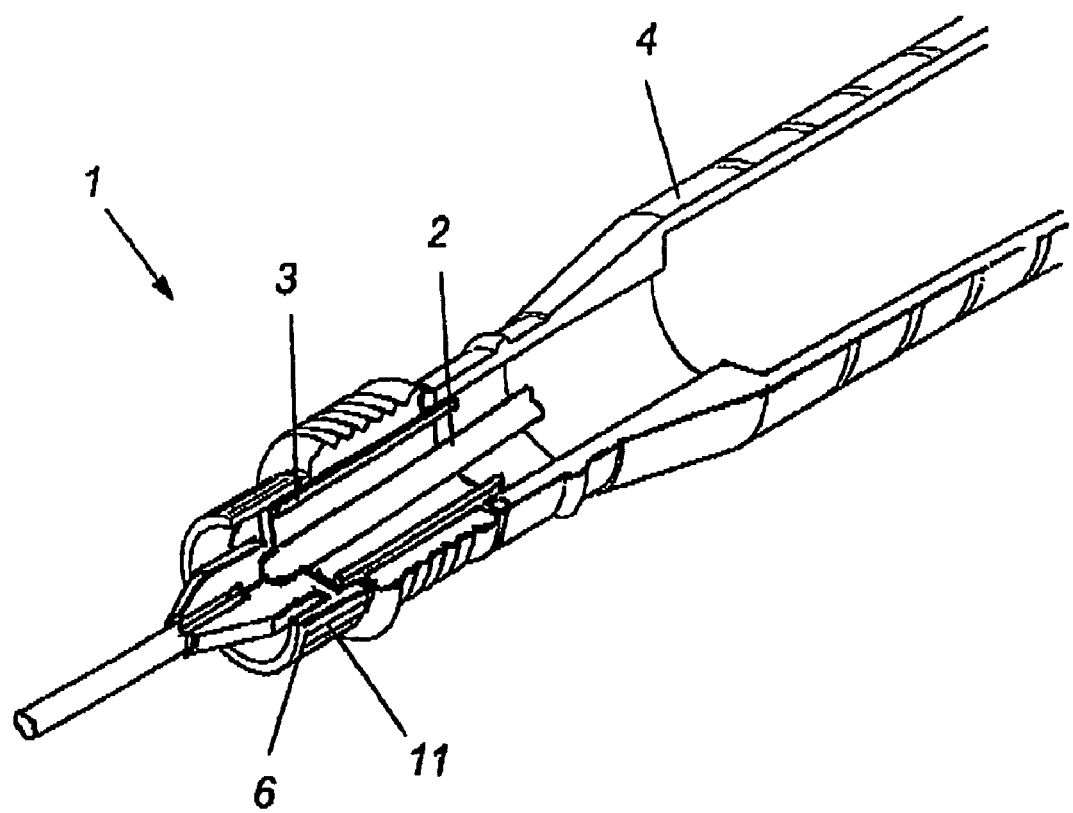
FIG. 1 shows a cross-sectional view through the coupling chamber of the invention.
Figures 2, 3:
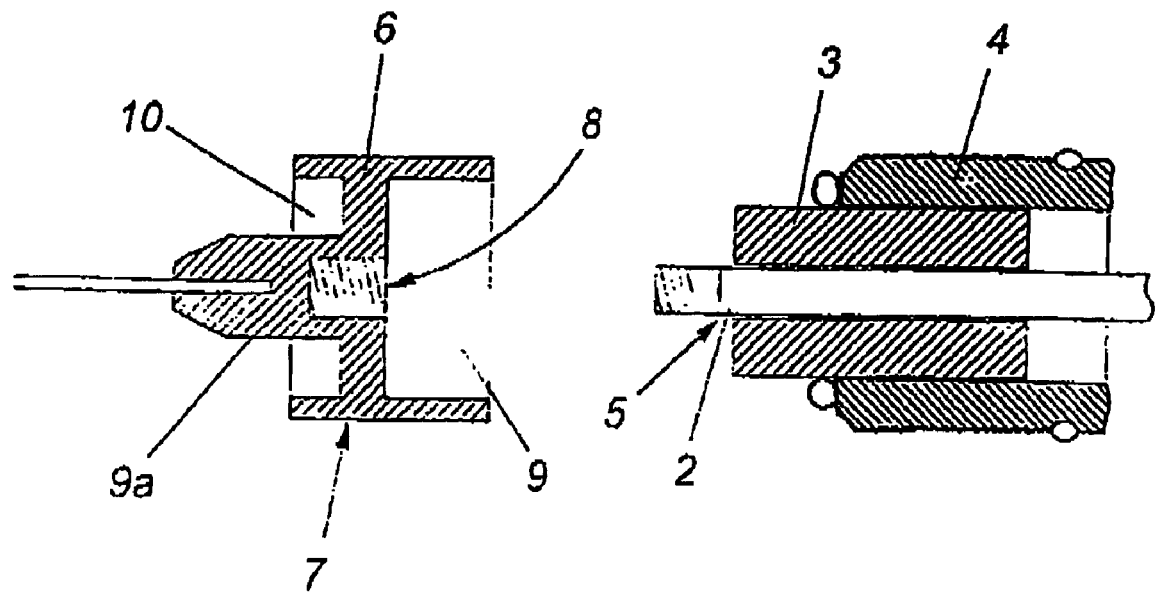
FIG. 2 shows a cross section through the base of the coupling needle of the invention.
FIG. 3 shows in detail the threaded bolt of the coupling of the invention.

The coupling 1 of the invention consists of a threaded bolt 2 emerging from a protruding cylindrical sleeve 3 of the casing 4 of the mechanized punch that generates the movement of the needle by means of a centered orifice 5 at the end thereof, and a needle base 6.

The bolt 2 screws into the needle base 6, which consists of a plastic body 7 with general disc-like form that constitutes a shield that prevents direct projection of fluids towards the orifice 5 of the sleeve 3.

One of the faces of the body 7 has a centered threaded orifice 8 for coupling to the bolt 2, while its borders are extended to form a skirt 9 of complementary overlap over sleeve 3.

On the opposite face, the body 7 has a protuberance 9a in a centered position protruding from where the body of the needle that cannot be disassembled is mounted, extending the borders 10 to form a housing that prevents diffusion of the fluids towards the end zone of the coupling to the bolt in cooperation with the skirt 9.

The outer perimeter part of the base 6 of the needle incorporates a ridge 11 in an axial direction that favors adherence with the fingers to screw in and/or unscrew the base of the needle of the bolt.

With the nature of the invention sufficiently described, as well as a practical embodiment thereof, it should be stated that the details of the aforementioned dispositions and presented in the attached drawings can be changed without altering the fundamental principle.

The invention claimed is:

1. Sanitary coupling for needle and mechanized punch for micropigmentation and tattooing, comprising a mechanized punch casing, a threaded bolt that can perform shuttle micromovements of a protruding section of the mechanized punch casing to which a base of a needle is operatively coupled, wherein the bolt passes through the mechanized punch casing through an orifice located in at least one of a sleeve in the casing; the base of the needle has a disc-like body with one face that presents a threaded orifice for coupling to the threaded bolt, and which has an edge extended to form a complementary overlapping skirt around the; and another face which is a protruding portion centered where a non-dismountable body of the needle is attached, with the edges of the disc-like body forming a housing for fluid collection.

2. Sanitary coupling for needle and mechanized punch for micropigmentation and tattooing according to claim 1 characterized in that the casing has a cylindrical form.

3. Sanitary coupling for needle and mechanized punch for micropigmentation and tattooing according to claim 1, characterized in that the base of the needle has a ridge on the outside perimeter that aids finger grip.

* * * * *